(12) United States Patent
Firoozabadi et al.

(10) Patent No.: US 9,919,160 B2
(45) Date of Patent: Mar. 20, 2018

(54) METHOD AND APPARATUS FOR SCORING THE RELIABILITY OF SHOCK ADVISORY DURING CARDIOPULMONARY RESUSCITATION

(71) Applicant: KONINKLIJKE PHILIPS N.V., Eindhoven (NL)

(72) Inventors: Reza Firoozabadi, Thousand Oaks, CA (US); Saeed Babaeizadeh, Arlington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/775,029

(22) PCT Filed: Mar. 12, 2014

(86) PCT No.: PCT/IB2014/059647
§ 371 (c)(1),
(2) Date: Sep. 11, 2015

(87) PCT Pub. No.: WO2014/141080
PCT Pub. Date: Sep. 18, 2014

(65) Prior Publication Data
US 2016/0015991 A1    Jan. 21, 2016

Related U.S. Application Data

(60) Provisional application No. 61/778,658, filed on Mar. 13, 2013.

(51) Int. Cl.
*A61N 1/39* (2006.01)
*A61B 5/00* (2006.01)
(Continued)

(52) U.S. Cl.
CPC ........ *A61N 1/3925* (2013.01); *A61B 5/04012* (2013.01); *A61B 5/053* (2013.01);
(Continued)

(58) Field of Classification Search
CPC . A61N 1/046; A61N 1/08; A61N 1/39; A61N 1/3925; A61N 1/3993; A61B 5/04012; A61B 5/053; A61B 5/7221
(Continued)

(56) References Cited

U.S. PATENT DOCUMENTS 5,511,553 A * 4/1996 Segalowitz .......... A61B 5/0006
128/903
5,571,142 A * 11/1996 Brown ................. A61N 1/3925
128/200.24
(Continued)

FOREIGN PATENT DOCUMENTS

EP         2172245 A1    4/2010
WO    2011040929 A1    4/2011

*Primary Examiner* — Christopher A Flory

(57) ABSTRACT

A method, system and device to detect and use clean ECG segments, which do not need filtering to remove artifact or CPR-induced noise, is described to provide a reliability score for the decision made by shock advisory algorithms. The method can be implemented in a system and/or device that is provided with a display for indicating to a user the relative quality of the determination of an electrotherapy analysis circuit.

18 Claims, 14 Drawing Sheets

(51) Int. Cl.
*A61B 5/04* (2006.01)
*A61B 5/053* (2006.01)

(52) U.S. Cl.
CPC .............. *A61B 5/7221* (2013.01); *A61N 1/39* (2013.01); *A61N 1/3993* (2013.01)

(58) Field of Classification Search
USPC .......................................... 607/4, 5, 7, 142
See application file for complete search history.

(56) References Cited

U.S. PATENT DOCUMENTS

| | | | |
|---|---|---|---|
| 6,438,419 B1* | 8/2002 | Callaway | A61N 1/3925 600/508 |
| 6,752,771 B2* | 6/2004 | Rothman | A61H 9/0078 601/44 |
| 7,567,837 B2 | 7/2009 | Weil et al. | |
| 7,822,471 B2 | 10/2010 | Bowers | |
| 8,509,881 B2 | 8/2013 | Thiagarajan et al. | |
| 9,409,034 B2 | 8/2016 | Babaeizadeh et al. | |
| 2003/0216785 A1* | 11/2003 | Edwards | A61N 1/3993 607/5 |
| 2005/0245974 A1* | 11/2005 | Sherman | A61B 5/046 607/5 |
| 2006/0025824 A1* | 2/2006 | Freeman | A61B 5/0464 607/5 |
| 2006/0173500 A1* | 8/2006 | Walker | A61B 5/046 607/5 |
| 2006/0173501 A1* | 8/2006 | Stickney | A61B 5/046 607/5 |
| 2006/0178865 A1* | 8/2006 | Edwards | A61N 1/39 704/1 |
| 2006/0235320 A1* | 10/2006 | Tan | A61B 5/0464 600/509 |
| 2007/0100379 A1* | 5/2007 | Tan | A61B 5/0464 607/2 |
| 2007/0129647 A1* | 6/2007 | Lynn | A61B 5/00 600/538 |
| 2007/0162076 A1* | 7/2007 | Tan | A61B 5/0464 607/5 |
| 2007/0191688 A1* | 8/2007 | Lynn | A61B 5/002 600/300 |
| 2007/0219588 A1* | 9/2007 | Freeman | A61H 31/005 607/5 |
| 2007/0299473 A1* | 12/2007 | Matos | A61N 1/0476 607/5 |
| 2008/0046020 A1* | 2/2008 | Peterson | A61N 1/37247 607/30 |
| 2008/0312708 A1* | 12/2008 | Snyder | A61N 1/39 607/5 |
| 2010/0106208 A1* | 4/2010 | Freeman | A61H 31/005 607/5 |
| 2010/0152300 A1 | 6/2010 | Walker et al. | |
| 2010/0152800 A1* | 6/2010 | Walker | A61B 5/046 607/5 |
| 2010/0292568 A1* | 11/2010 | Droitcour | A61B 5/05 600/425 |
| 2010/0324612 A1* | 12/2010 | Matos | A61N 1/0476 607/4 |
| 2011/0034816 A1* | 2/2011 | Tan | A61B 5/0464 600/509 |
| 2011/0008237 A1 | 4/2011 | Sullivan | |
| 2011/0105930 A1 | 5/2011 | Thiagarajan et al. | |
| 2011/0106190 A1* | 5/2011 | Foeller | A61N 1/39 607/5 |
| 2011/0130798 A1* | 6/2011 | Elghazzawi | A61N 1/3925 607/5 |
| 2011/0202100 A1* | 8/2011 | Tan | A61H 31/005 607/6 |
| 2011/0202101 A1* | 8/2011 | Tan | G09B 23/288 607/7 |
| 2011/0224746 A1 | 9/2011 | Didon | |
| 2012/0010543 A1* | 1/2012 | Johnson | A61N 1/3925 601/41 |
| 2012/0022606 A1* | 1/2012 | Walker | A61B 5/046 607/3 |
| 2012/0179234 A1* | 7/2012 | Carrington | A61N 1/046 607/142 |
| 2012/0226178 A1* | 9/2012 | Freeman | A61B 5/0464 600/510 |
| 2013/0138168 A1* | 5/2013 | Quan | A61N 1/3925 607/6 |
| 2013/0144181 A1* | 6/2013 | Fogt | A61B 5/02405 600/521 |
| 2013/0296727 A1* | 11/2013 | Sullivan | A61B 5/046 600/513 |
| 2014/0100497 A1* | 4/2014 | Hayashi | A61B 5/04012 601/41 |
| 2014/0107541 A1* | 4/2014 | Sullivan | A61B 5/7217 601/41 |
| 2014/0213941 A1* | 7/2014 | Johnson | A61N 1/3925 601/41 |
| 2014/0228695 A1* | 8/2014 | Tan | A61B 5/0464 600/509 |
| 2014/0236030 A1* | 8/2014 | Tan | A61B 5/0464 600/509 |
| 2014/0277224 A1* | 9/2014 | Quan | H01L 23/53238 607/6 |
| 2014/0277225 A1* | 9/2014 | Quan | A61N 1/3987 607/6 |
| 2014/0277228 A1* | 9/2014 | Quan | A61N 1/3987 607/7 |
| 2014/0342331 A1* | 11/2014 | Freeman | G09B 23/288 434/265 |
| 2014/0350617 A1* | 11/2014 | Jorgenson | A61N 1/3987 607/6 |
| 2015/0018695 A1* | 1/2015 | Tan | A61H 31/005 600/484 |
| 2015/0045686 A1* | 2/2015 | Lynn | A61B 5/00 600/531 |
| 2015/0046175 A1* | 2/2015 | Jorgenson | A61N 1/3925 705/2 |
| 2015/0112401 A1* | 4/2015 | Sullivan | A61B 5/7217 607/5 |
| 2015/0165223 A1 | 6/2015 | Babaeizadeh et al. | |
| 2015/0257715 A1* | 9/2015 | Quan | A61B 5/7257 600/510 |
| 2015/0297107 A1* | 10/2015 | Sullivan | A61N 1/3925 600/523 |
| 2015/0352367 A1* | 12/2015 | Quan | A61N 1/3925 601/41 |
| 2016/0015990 A1* | 1/2016 | Helfenbein | A61N 1/39 600/523 |
| 2016/0015991 A1 | 1/2016 | Firoozabadi et al. | |
| 2016/0059026 A1* | 3/2016 | Jorgenson | A61N 1/3925 607/6 |
| 2016/0082278 A1* | 3/2016 | Quan | A61N 1/3987 607/7 |
| 2016/0150977 A1* | 6/2016 | Tan | A61H 31/005 600/301 |
| 2016/0213559 A1* | 7/2016 | Schiller | A61H 31/006 |

\* cited by examiner

500

| CC on current segment? | Current segment shockable? | Last RS | CC on previous segment? | Previous segment shockable? | Is this the first segment? | Update on RS |
|---|---|---|---|---|---|---|
| Yes | N/A | R ≠ 0 | N/A | N/A | No | R > 0: R = R - 1<br>R < 0: R = R + 1 |
| Yes | N/A | R = 0 | N/A | N/A | No | R = 0 |
| No | No | N/A | N/A | N/A | Yes | R = -3 |
| No | Yes | N/A | N/A | N/A | Yes | R = -3 |
| No | Artifact | N/A | N/A | N/A | Yes | R = 0 |
| No | No | R = 0 | N/A | N/A | No | R = -3 |
| No | No | R ≠ 0 | No | Yes | No | R = R -7 |
| No | No | R ≠ 0 | No | No | No | R = R -1 |
| No | No | R ≠ 0 | Yes | N/A | No | R = R -7 |
| No | No | R ≠ 0 | No | Artifact | No | R = R -7 |
| No | Yes | R = 0 | N/A | N/A | No | R = 3 |
| No | Yes | R ≠ 0 | No | Yes | No | R = R + 7 |
| No | Yes | R ≠ 0 | No | No | No | R = R + 1 |
| No | Yes | R ≠ 0 | Yes | N/A | No | R = R + 7 |
| No | Yes | R ≠ 0 | No | Artifact | No | R = R + 7 |

FIG. 5

METHOD AND APPARATUS FOR SCORING THE RELIABILITY OF SHOCK ADVISORY DURING CARDIOPULMONARY RESUSCITATION

This application is a national stage application under 35 U.S.C. § 371 of International Application No. PCT/IB2014/059647 filed Mar. 12, 2014 and published in the English language on Sep. 18, 2014 as International Publication No. WO/2014/141080, which claims priority to U.S. Application No. 61/778,658 filed on Mar. 13, 2013, the entire disclosures of which are incorporated herein by reference.

The invention relates generally to an improved method, system and device for monitoring a subject cardiac rhythm during the application of cardio-pulmonary resuscitation (CPR). More particularly, the invention relates to a medical device which incorporates an improved diagnostic algorithm/method that analyzes patient physiological data during CPR and scores the reliability of a determination whether an electrotherapy shock is indicated. If the device is a defibrillator, the reliability scoring provides user guidance and/or controls the device electrotherapy circuit based on the determination.

Sudden cardiac arrest (SCA) is a leading cause of death in the United States. In about 40% of sudden cardiac arrest (SCA) patients, the initial cardiac rhythm observed is ventricular fibrillation (VF). CPR is the protocol treatment for SCA, which includes chest compressions and ventilations that provide circulation in the patient. Defibrillation is interposed between sessions of CPR in order to treat underlying VF. It is generally known that the probability of successful defibrillation diminishes as the interval between the end of CPR compressions and the delivery of a defibrillating shock increases. Conversely, shortening the interval between the last compression and the shock by even a few seconds can improve shock success (defibrillation and return of spontaneous circulation (ROSC)).

Furthermore, defibrillation generally does not terminate the underlying causes of VF even if it temporarily corrects the VF. Thus, the underlying causes may induce a recurrence of VF following defibrillation. This phenomenon is known as refibrillation. The present common recommendation is to immediately resume chest compressions after the shock delivery for 2 minutes before analyzing the cardiac rhythm again. Some resuscitation thought leaders, however, believe that it is more beneficial to deliberately interrupt CPR early to deliver a shock aimed at correcting refibrillation.

Defibrillators deliver a high-voltage impulse to the heart in order to restore normal rhythm and contractile function in patients who are experiencing arrhythmia, such as VF or ventricular tachycardia (VT) that is not accompanied by spontaneous circulation. There are several classes of defibrillators, including manual defibrillators, implantable defibrillators, and automatic external defibrillators (AEDs). AEDs differ from manual defibrillators in that AEDs can automatically analyze the ECG rhythm to determine if defibrillation is necessary.

FIG. 1 is an illustration of a defibrillator 10 being applied by a user 12 to resuscitate a patient 14 suffering from cardiac arrest. In sudden cardiac arrest, the patient is stricken with a life threatening interruption to the normal heart rhythm, typically in the form of VF or VT that is not accompanied by spontaneous circulation (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient will likely die. Conversely, the quicker that circulation can be restored (via CPR and defibrillation) after the onset of VF, the better the chances that the patient 14 will survive the event. The defibrillator 10 may be in the form of an AED capable of being used by a first responder. The defibrillator 10 may also be in the form of a manual defibrillator for use by paramedics or other highly trained medical personnel.

According to an exemplary embodiment of the present disclosure, electrodes 16 are applied across the chest of the patient 14 by the user 12 in order to acquire an ECG signal from the patient's heart. The defibrillator 10 then analyzes the ECG signal for signs of arrhythmia. If VF is detected, the defibrillator 10 signals the user 12 that a shock is advised. After detecting VF or other shockable rhythm, the user 12 then presses a shock button on the defibrillator 10 to deliver defibrillation pulse to resuscitate the patient 14. Defibrillator 10 can also signal the user 12 via visual and audible prompts as to when to start and stop periods of CPR compressions.

In addition to detecting ECG voltages, defibrillator 10 can also independently measure the patient's transthoracic impedance via the patient electrodes 16 in order to adjust the parameters of the defibrillating shock accordingly. Variations in the impedance measurement can also be used to determine the extent of patient motion, such as that caused by CPR chest compressions (CC). In other defibrillators (not shown), a separate CPR sensing device, such as an accelerometer or force sensor, can be used to provide an indication of ongoing CPR. If the defibrillator is integrated to an automated CPR machine, a compressions status signal from the machine can provide a CPR indication.

In currently available AEDs, the ECG analysis typically must be conducted during a non-CPR hands-off period because the electrical artifact induced by CPR-related motion tends to make the analysis algorithm unreliable. If the AED erroneously makes a false "shock" determination because of the artifact, it may enable the delivery of a shock potentially fatal to the patient. Thus, an adverse seconds-long interval between the end of CPR and the delivery of the shock impulse is generally thought to be necessary to provide for a clean analysis. For the same or similar reasons, existing AED shock analysis algorithms are generally unable to detect and allow treatment for early refibrillation that occurs during CPR.

A number of methods have been developed in an attempt to determine an accurate ECG measurement during CPR chest compressions. For example, U.S. Application No. 61/654,143, entitled "Method and Apparatus for Analyzing Cardiac Rhythm During CPR", filed Jun. 1, 2012, teaches, e.g., methods which utilize filtering chest compression artifact to allow a reliable AED diagnosis during CPR. U.S. Patent Publication 2011/0105930 A1 entitled "TRUE ECG MEASUREMENT DURING CARDIO PULMONARY RESUSCITATION BY ADAPTIVE PIECEWISE STITCHING ALGORITHM" describes, e.g., using a filter to remove CPR artifact from the ECG. Similarly, International Publication WO 2011/040929 A1, entitled "DECIDING ON PATIENT ELECTRIC SHOCK THERAPY", describes, e.g., a method for removing CPR artifact from an ECG prior to deciding as to whether to administer a shock to the patient. Another example, U.S. Pat. No. 7,567,837 entitled "ENHANCED RHYTHM IDENTIFICATION IN COMPRESSION CORRUPTED ECG" describes, e.g., a method for identifying and removing CPR artifact by presuming that the artifact is a high amplitude signal, while the ECG is any low amplitude signal found between successive high amplitude signals. Further, International Publication WO 2006/

015348 A2 entitled "DETECTING ARTIFACT SIGNALS CAUSED BY CPR OR PATIENT MOTION" describes, e.g., a method for detecting the presence of CPR artifact in an ECG signal, but no attempt appears to be offered to obtain an accurate ECG from the contaminated signal.

But reducing hands-off intervals by filtering chest compressions (CC) artifact during CPR can have limitations. One of such limitations is that usually these techniques need one or more reference signals other than ECG to be able to filter the CC artifact. Acquisition of such signals may imply altering the AED hardware. Most current AEDs only record the surface ECG signal to diagnose the underlying heart rhythm, and in some cases, a limited set of reference channels to improve CPR administration and the delivery of the defibrillation shock. Another limitation is that no known filtering technique is perfect. No matter how good the filtering is, there will almost always be at least some residuals left on the ECG which could potentially lead to incorrect determination of the underlying rhythm by the AED shock advisory algorithm. During non-shockable rhythms, in particular asystole, such imperfect filtration of the CC artifact could make the shock advisory algorithm to erroneously call the rhythm shockable because the residuals may look like VF to the algorithm. On the other hand, for shockable rhythms such as VF, the filtering technique may mistakenly filter out some of the VF information which may consequently make the rhythm look non-shockable to the shock advisory algorithm. In summary, none of the previously known techniques have been shown to provide a generally acceptable satisfactorily accurate ECG from which an adequately reliable shock decision can be made.

What is needed therefore to address and overcome the deficiencies described herein above, for example, is an improved method, system and device for analyzing an underlying cardiac rhythm in the presence of CPR.

As described, rhythm analysis during hands-off intervals (when there is no CC artifact to filter) is generally more reliable than rhythm analysis during CPR after filtering the CC artifact. Although minimizing hands-off intervals is recommended, in practice the rescuer may frequently interrupt chest compression during CPR. Some of such interruptions are to check the ECG rhythm, but there are other reasons as well. For example, the rescuer may interrupt CC to check for pulse, move the patient, or perform other tasks. Exemplary embodiments of methods, systems and devices in accordance with the present invention can actively look for such clean segments in the ECG waveform and analyze them to have an accurate sense of the underlying rhythm when its indication is needed, for example, at the end of 2-minute CC protocol when the rescuer is ready to deliver a shock if advised. After the rhythm is known by analyzing a clean segment, the rhythm is more likely to change by longer time passing. Therefore, the reliability of the rhythm type tends to decrease over time without finding a new clean segment to analyze. A scoring method is thus adopted which provides a measure which takes into account both the elapsed time from the last hands-off interval and the shock decision in that interval. The measure moves towards zero as time elapses from the most recent hands-off interval. The sign of this measure indicates the shockability (positive) or non-shockability (negative) of the underlying cardiac rhythm. One advantage of the scoring method is that it is computationally efficient and can be used either stand-alone or in conjunction with other exemplary methods and techniques such as described in U.S. Application No. 61/654,143, entitled "Method and Apparatus for Analyzing Cardiac Rhythm During CPR", filed Jun. 1, 2012, the entire disclosure of which is hereby incorporated herein by reference.

In addition, exemplary embodiments of the method, system and device according to the present invention can support the decision made by virtually any shock advisory system by providing a reliability score (RS). The RS can potentially improve the quality of CPR by enhancing the performance of the shock advisory algorithm.

The RS in a preferred embodiment of the present invention is calculated at the end of each ECG segment and is assigned an integer number, e.g., between −6 and +6. Of course, the scope of the invention is not limited to these particular numbers.

In accordance with exemplary embodiments of the present invention, a method, system and device/apparatus are described which can increase the accuracy of the shock advisory during CPR by harnessing the information found in the portions of the ECG signal which are clean and do not need filtering. Exemplary embodiments of the present invention can provide an indication of the reliability of the decision to provide, or not to provide, electrotherapy. For example, an exemplary embodiment of a method according to the present invention can comprise the steps of obtaining two or more time-sequential ECG data sets, acquiring two or more corresponding time-sequential CPR reference signal data sets, detecting the presence of CPR-related noise on each of the ECG data sets, analyzing each of the ECG data sets and classifying them as a "shock" advice or a "no-shock" advice, determining the reliability of the most recent ECG advice based on the analyzing step and the detecting step, and automatically issuing a shock decision and a reliability score based on the classifying step and the determining step. The exemplary method can further use the result of the comparison step to issue an operational command to a medical device such as a defibrillator to provide further guidance to the operator or to modify the device operating protocol.

It is yet another object of the present invention to describe a medical device which incorporates an improved ECG analysis method in accordance with the present invention that accurately analyzes ECG in the presence of CPR artifact, and provides a reliability indicator of the analysis. In accordance with the present invention, the device can be a defibrillator or an AED. The exemplary device can comprise a front end operable to obtain two or more time-sequential ECG data sets, an input operable to acquire two or more corresponding time-sequential CPR reference signal data sets, a chest compression detector, a shock advisory algorithm module which analyzes and classifies each of the ECG data sets as a shock or no-shock advice, a reliability analyzer which determines the reliability of the most recent advice, a shock decision generator which uses the advice and the reliability indicator to generate a shock decision, and an output generator for issuing a user indication of the shock decision and its reliability. The device can thus operate to give the user a more informative indication of the robustness of the analysis method/algorithm, and can be optionally configured to act to automatically modify the device operating protocol.

It is yet another object of the present disclosure to describe a defibrillator in accordance with the present invention which, e.g., incorporates the previously-described objects of the present invention. For example, the exemplary defibrillator can comprise a host circuit which can analyze an ECG segment to determine whether electrotherapy is indicated, and a reliability analyzing circuit which can determine the reliability of the host circuit determination.

The exemplary defibrillator can also include a display which can indicate the reliability, preferably with a simple and easy-to-discern graphic icon, for example.

In accordance with exemplary embodiments of the present invention, the calculated RS falls into one of three reliability zones or segments, as shown in, e.g., FIG. 11. For example, values between −6 and −4 indicate that a no-shock advice arrived at by a shock advisory algorithm is reliable, e.g., the more negative the RS value, the more reliable is the no-shock advice. Values between −3 and 3 represent unreliability, with more negative values indicating more unreliable 'shock' advices, and more positive values indicating more unreliable 'no-shock' advices. An RS of 0 indicates an indeterminate condition. Values between +4 and +6 represent that a shock advice arrived at by a shock advisory algorithm is reliable, e.g., the more positive the RS value, the more reliable is the shock advice.

According to exemplary embodiments of the present invention, the RS score is intended to be used, e.g., with the output of the core shock-advisory algorithm. Outputs which are compatible with a zone of reliability ('shock' output with an RS in the shock reliability zone, and a 'no-shock' output with an RS in the no-shock reliability zone) are considered to be 'reliable'. Otherwise, the algorithm output is considered 'unreliable'. If the scoring method is integrated to a host defibrillator, the host decision module may integrate the reliability score as a key parameter in the final automated shock decision.

It is to be understood that the scope of the invention encompasses devices and systems which can have the described host computer functions and reliability analyzer functions implemented with or without additional hardware added to the device, e.g., in one or more software modules embodied in computer readable and/or computer executable instructions that can be stored on/in a computer or other digital memory hardware and/or storage device, and read and/or executed by a computer or other digital hardware processor or processing device.

IN THE DRAWINGS

FIG. 3a, FIG. 3b, FIG. 3c, and FIG. 3d together provide an exemplary illustration of a basic flow diagram for a method of analyzing ECG during CPR.

Figure 4A:
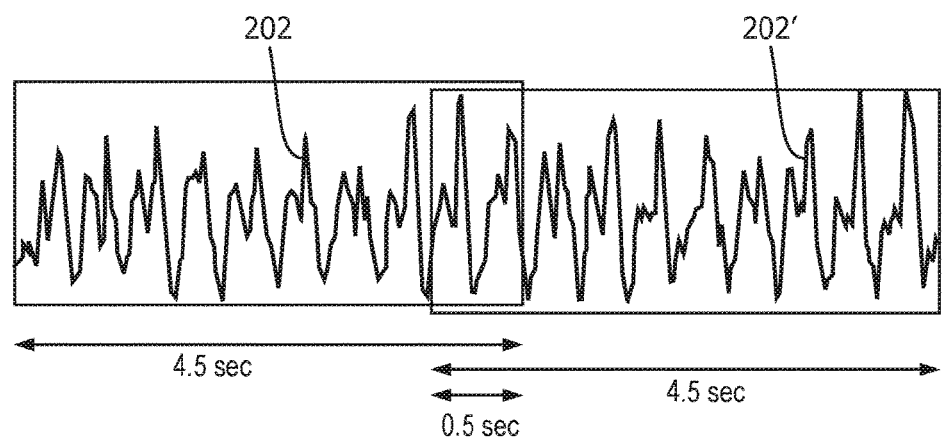
Figure 4B:
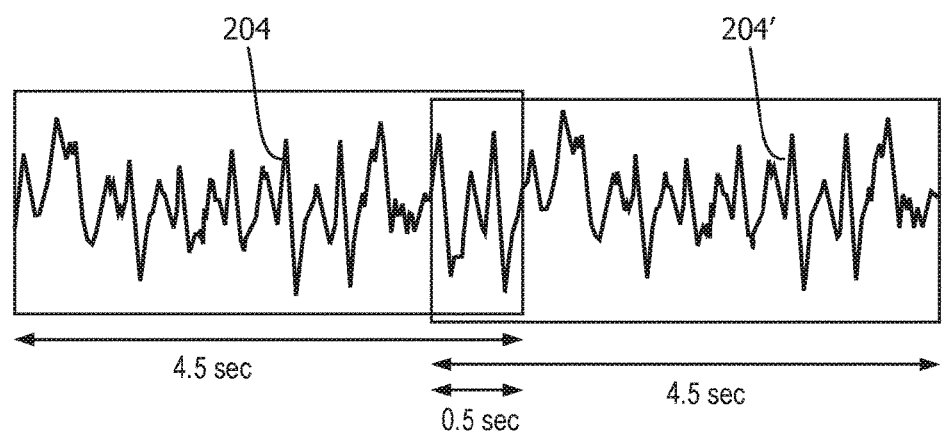

FIG. 4a is an exemplary illustration of a pair of time-sequenced ECG data sets according to an exemplary embodiment of the present invention. FIG. 4b is an exemplary illustration of a pair of time-sequenced CPR reference signal data sets, which also correspond in time to the FIG. 4a ECG data sets, in accordance with an exemplary embodiment of the present invention.

FIG. 5 is an exemplary illustration of a logical truth table according to an exemplary embodiment of a method in accordance with the present invention, showing, e.g., the interaction of detected parameters leading to a reliability decision.

Figure 6:
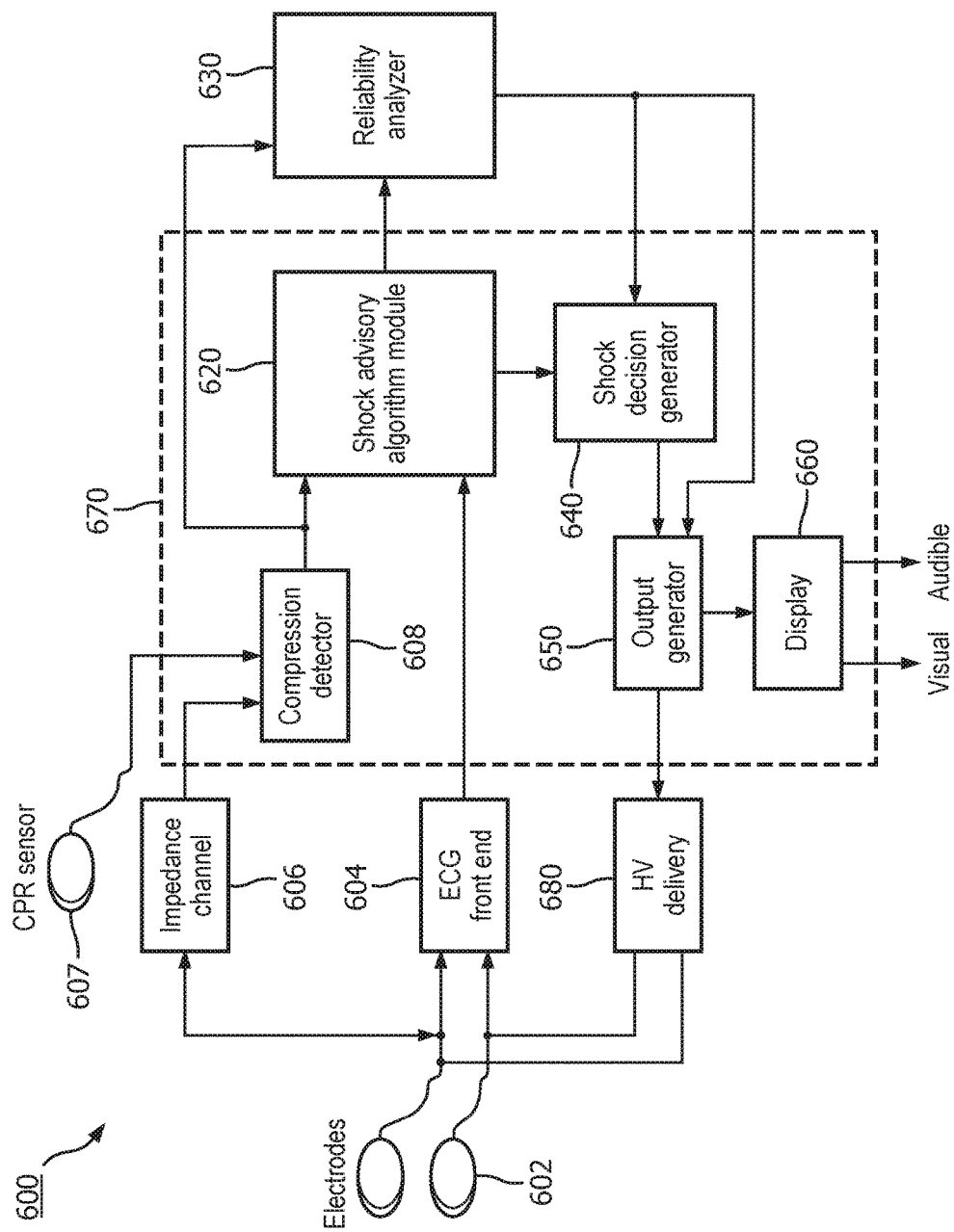

FIG. 6 is an exemplary illustration of a function block diagram of an exemplary embodiment of an apparatus according to the present invention.

Figure 7:
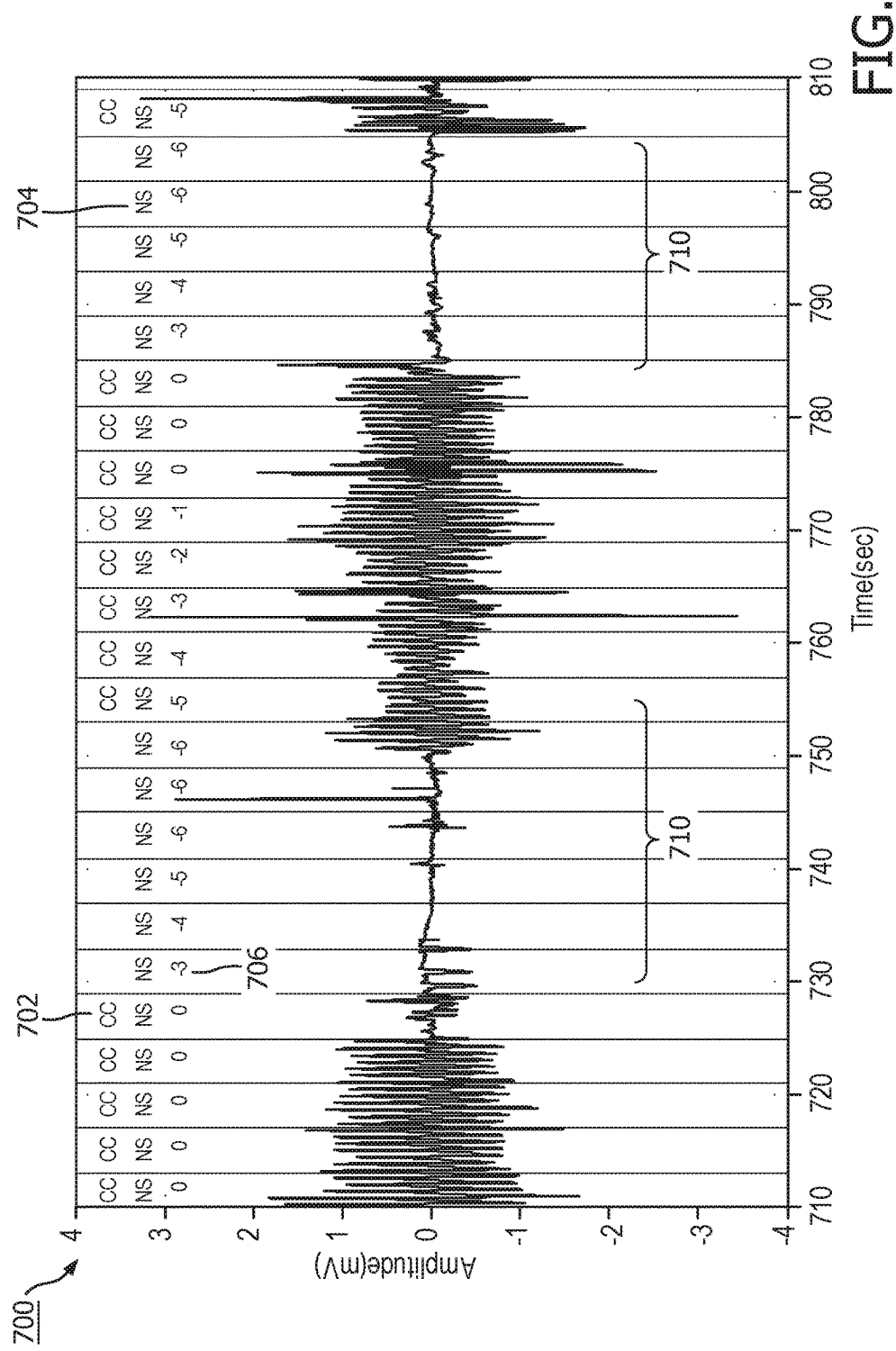

FIG. 7 illustrates an example of the operation of an exemplary embodiment of the present invention during the administration of CPR.

Figure 8:
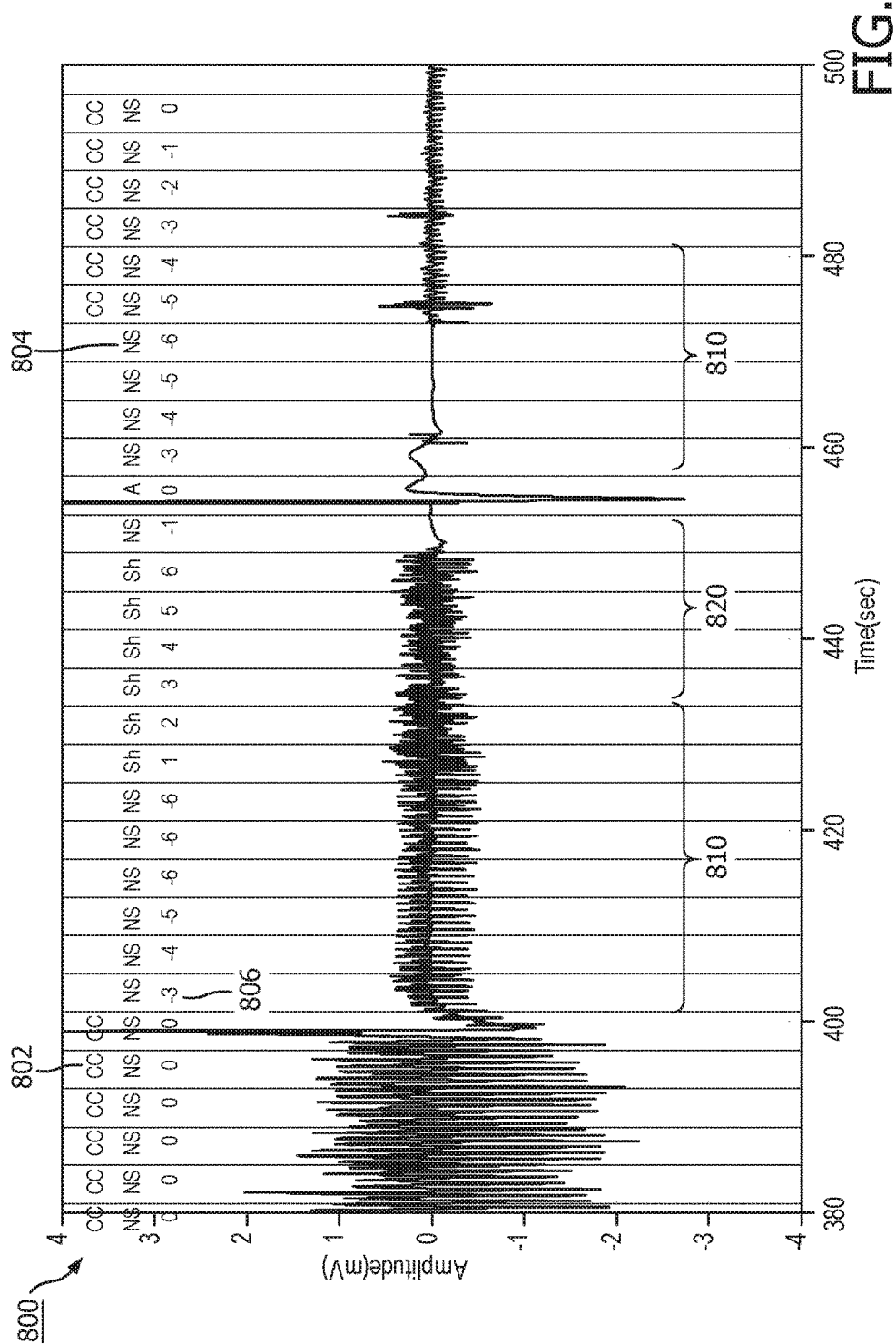

FIG. 8 illustrates another example of the operation of an exemplary embodiment of the present invention during and after the administration of CPR.

Figure 9:
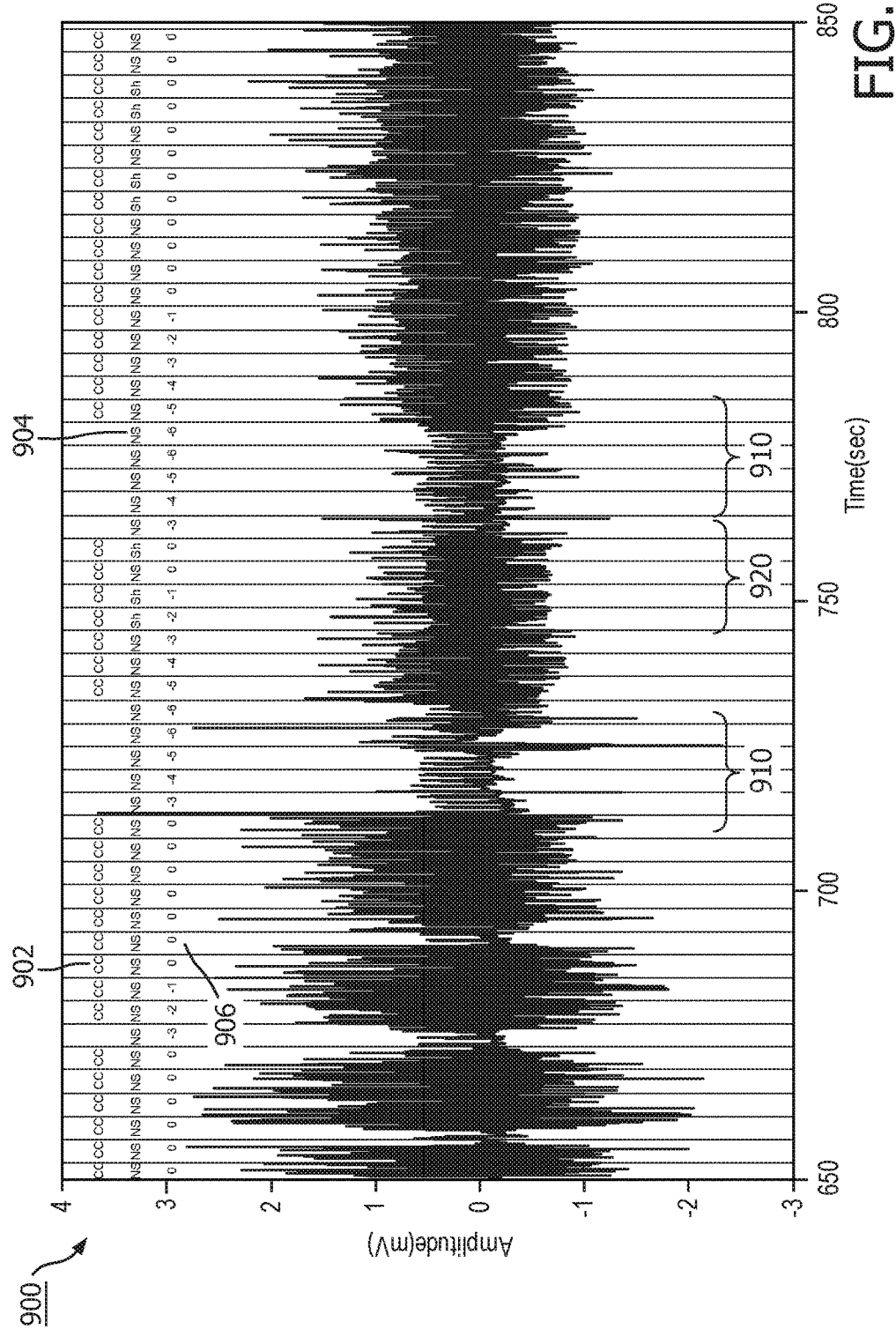

FIG. 9 illustrates yet another example of the operation of an exemplary embodiment of the present invention during the administration of CPR.

Figure 10:
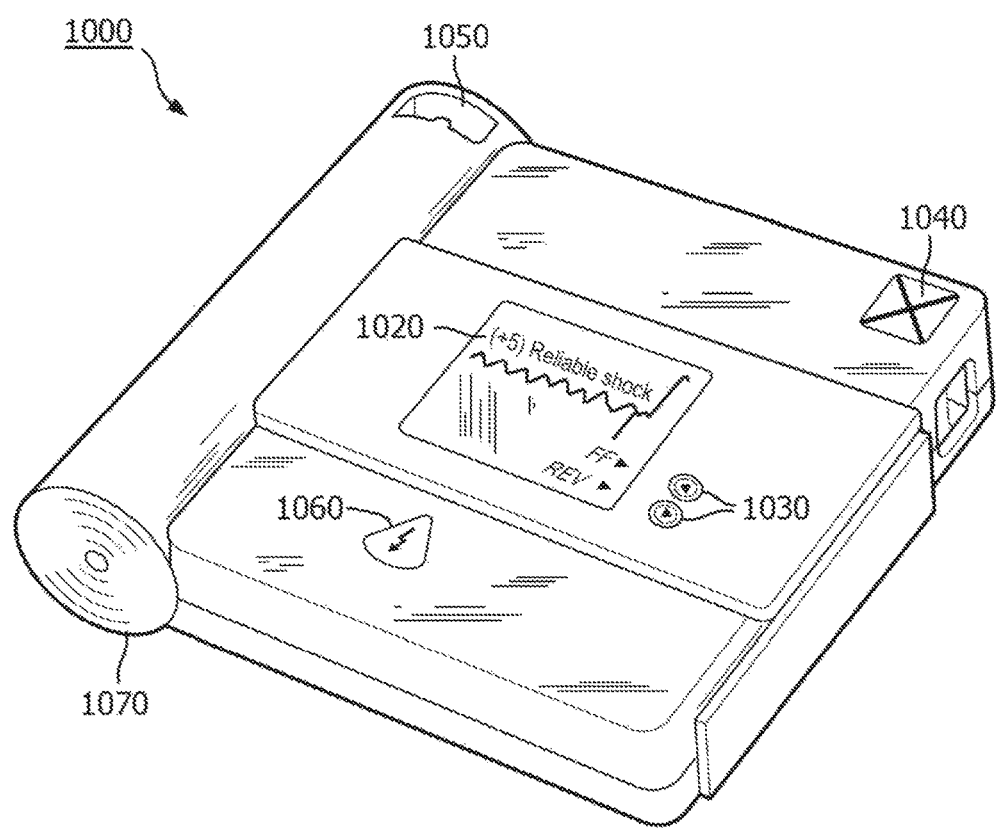

FIG. 10 illustrates a defibrillator embodiment of an apparatus in accordance with exemplary embodiments of the present invention.

Figure 11A:
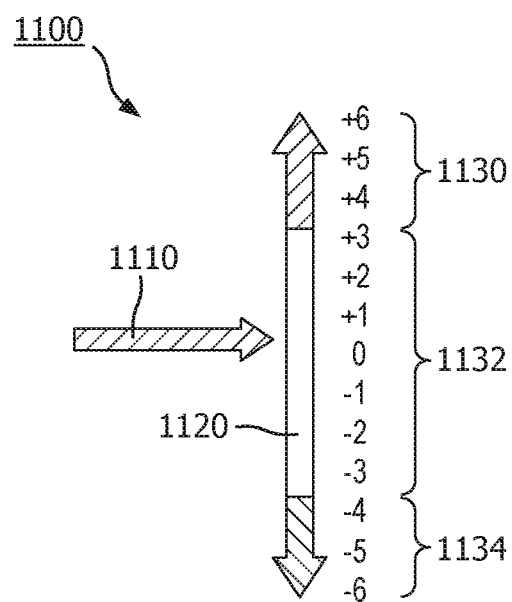
Figure 11B:
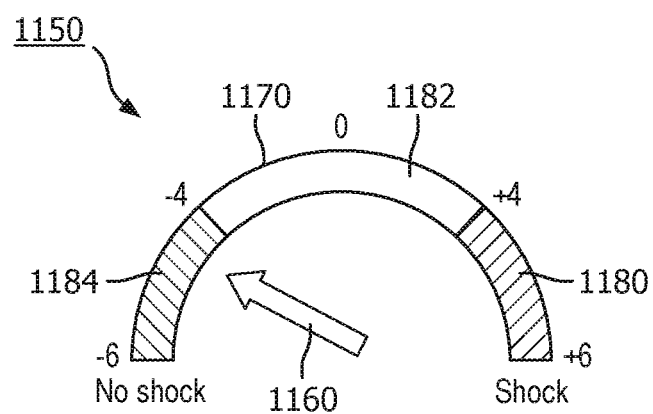

FIG. 11a and FIG. 11b illustrate two exemplary embodiments of the reliability score display in accordance with the present invention.

Figure 1:
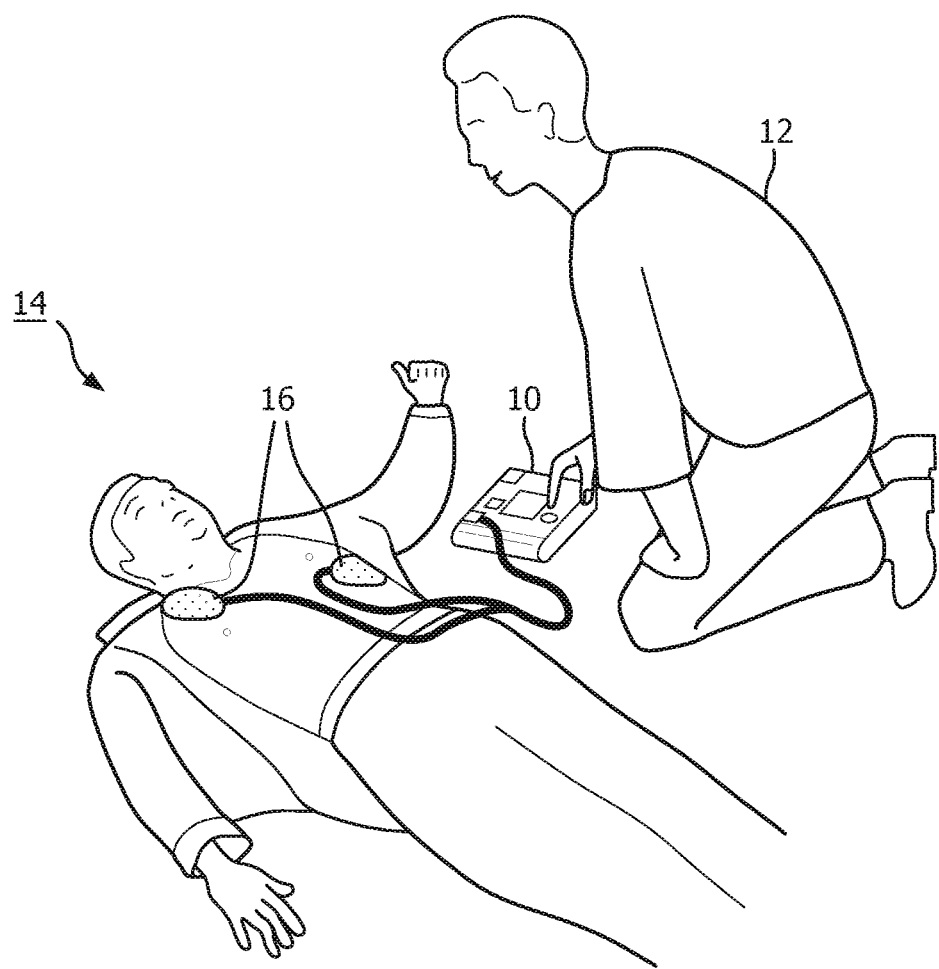
FIG. 1 is an exemplary illustration of a defibrillator which is in use with a patient suffering from cardiac arrest.
Figure 2:
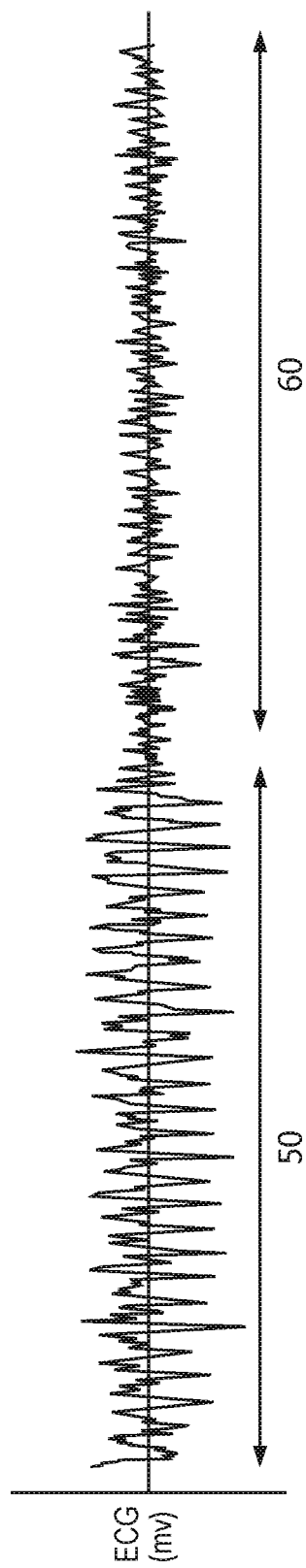
FIG. 2 is an exemplary illustration of a recording of a typical ECG, showing an ECG strip with CPR-induced artifact followed by an ECG strip without artifact.

With further reference to the figures, FIG. 2 illustrates an exemplary 23-second ECG strip from a subject patient whose underlying cardiac rhythm is VF. The first half (left hand side 50) of the waveform is recorded during CPR, and the second half (right hand side 60) is recorded after CPR has been paused, e.g., there is no chest compressions artifact on the ECG data. It can be seen that, during CPR at left hand side 50, the chest compression artifact induced on the ECG masks the underlying VF rhythm. A previously known shock advisory algorithm as applied to left hand side 50 might evaluate the CPR artifact as a regular ECG rhythm and erroneously determine that no shock is advised. This situation contrasts with an evaluation of the right hand side 60 waveform having no CPR artifact. There, a shock advisory algorithm can accurately detect the VF rhythm and properly advise a shock. Thus, FIG. 2 illustrates a problem with obtaining accurate ECG readings during CPR compressions that are ongoing during the rescue. FIG. 2 also illustrates that existing shock advisory algorithms would likely be unable to detect whether an ECG rhythm changes from a VF to a normal sinus rhythm or vice versa, i.e. refibrillation.

A basic solution to the identified problem is illustrated for example by the exemplary method flow chart encompassed by FIG. 3a, FIG. 3b, FIG. 3c, and FIG. 3d. The exemplary flow chart illustrates the detailed reliability score update procedure for a stream of ECG segments in an ECG in accordance with an exemplary embodiment of the present invention.

In accordance with exemplary embodiment of the present invention, in general, the RS remains in the unreliability zone until a 'shock' or a 'no-shock' advice is made by the core shock-advisory algorithm, after which the RS is updated in the corresponding direction: positive for 'shock' and negative for 'no-shock'. It is intended that subsequent decisions of the same type move the reliability score to the reliability zone in the same direction until it reaches the scoring limit of +/−6, for example. Any sudden shock advice in the opposite direction, e.g. from a shock to a no-shock, will temporarily move the score into the unreliability zone until the subsequent set of advices move it out of the unreliability zone in either direction. With the start of chest compressions, the reliability score moves towards zero and enters the unreliability zone. Any other type of artifact can be treated like a chest compression and move the score towards zero as well.

The exemplary embodiment of a method illustrated in FIG. 3 requires two types of data. For example, the first type is raw ECG data, digitized and arranged into sets by segments of predetermined duration. The ECG data need not be filtered prior to input. FIG. 4a illustrates a preferred arrangement of ECG data, wherein a first ECG data set 202 is 4.5 seconds long, and a second unfiltered ECG data set 202' overlaps with the first ECG data set 202 by 0.5 seconds. It should be understood by one having ordinary skill in the art in view of the teachings herein, however, that the scope of the present invention includes data segments having different lengths, different overlaps, no overlap at all, or being separated in time, for example. FIG. 3a illustrates the input of the corresponding time-sequential ECG data sets 202, 202' into the method 100 at the obtaining step 110.

Figure 3A:
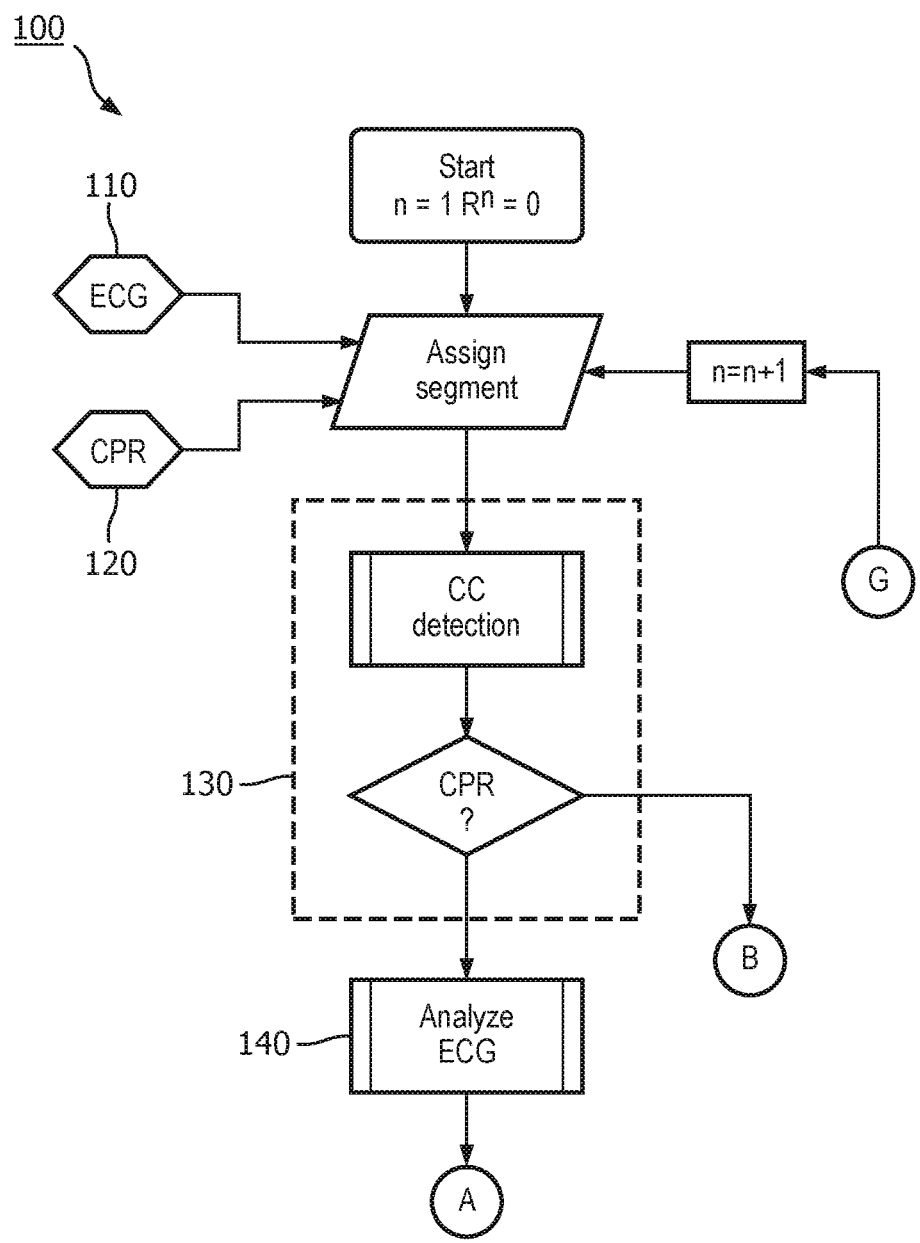
Figure 3B:
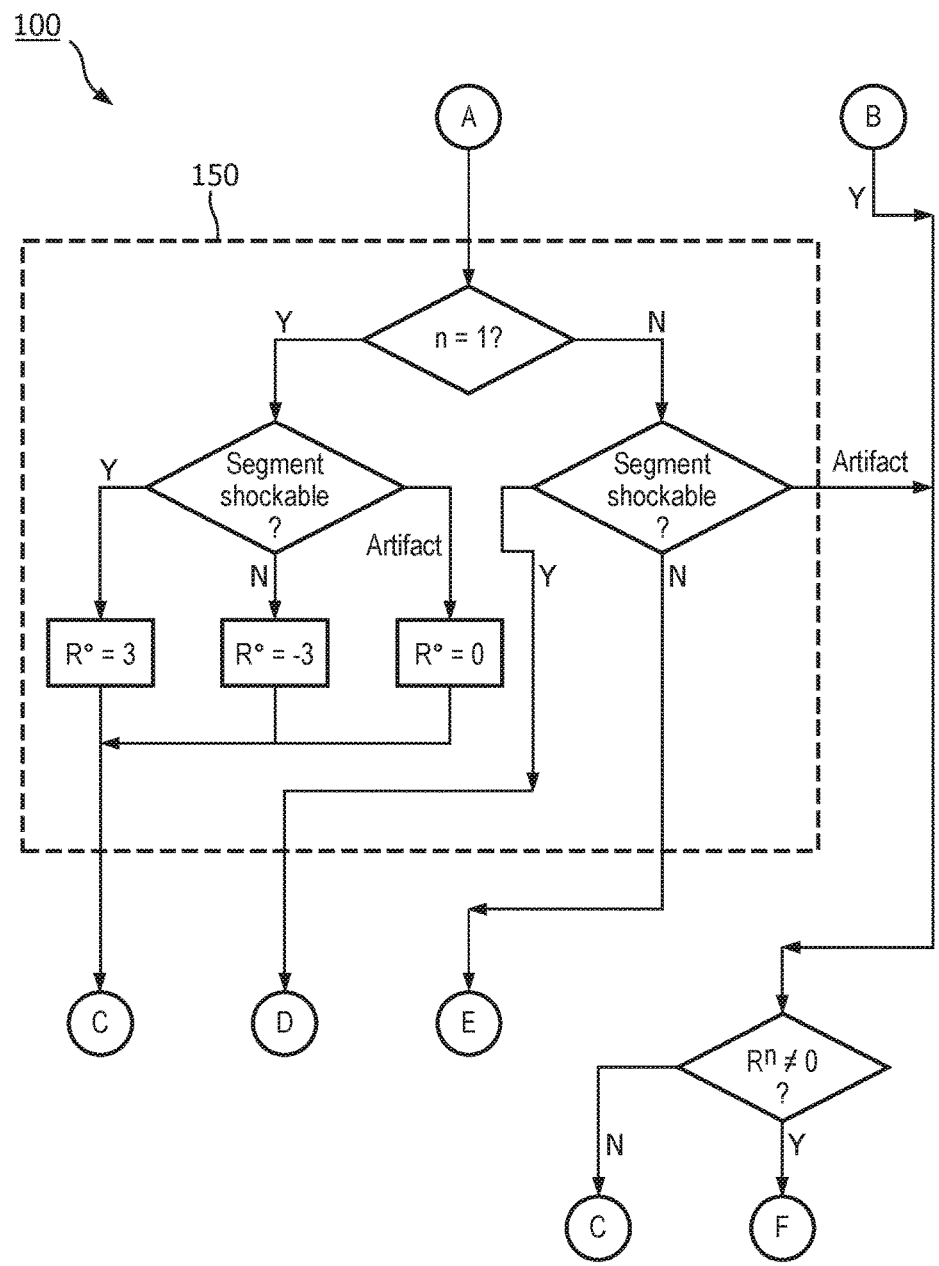
Figure 3C:
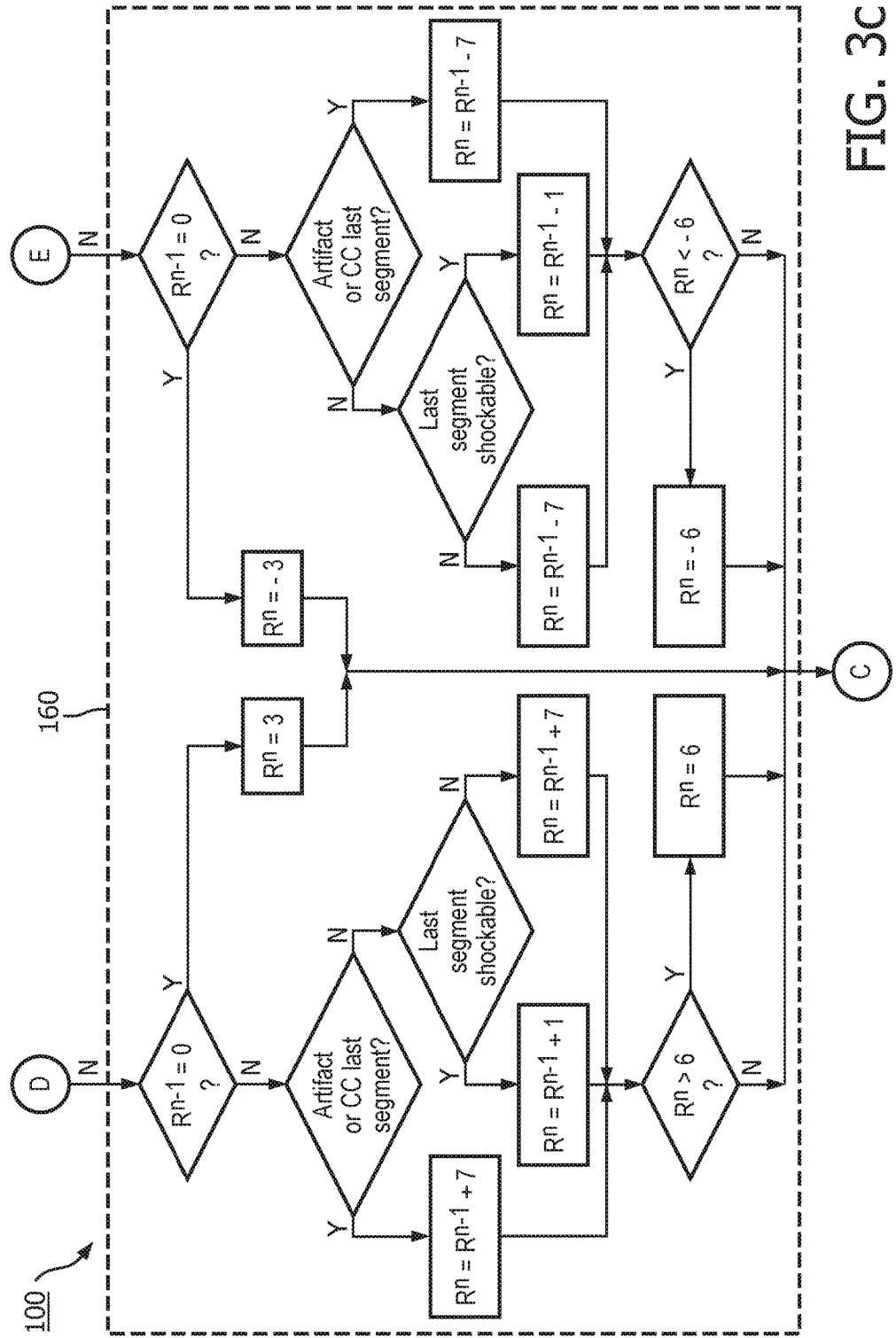

Further, in accordance with exemplary embodiments of the present invention, the second type of data can comprise or consists of CPR reference signal data, which is also arranged into sets by segments of predetermined duration. FIG. 4b illustrates a preferred arrangement of CPR data, wherein a first CPR reference signal data set 204 is 4.5 seconds long, and a second CPR reference signal data set 204' overlaps with the first CPR data set 204 by 0.5 seconds. Each CPR reference signal data set corresponds in time with the respective unfiltered ECG data set. Thus it should also to be understood by one having ordinary skill in the art in view of the teachings herein that the scope of the invention includes CPR data segments having different lengths, different overlaps, no overlap at all, or being separated in time, for example. FIG. 3a illustrates the input of the corresponding time-sequential CPR data sets 204, 204' into the method 100 at the acquiring step 120.

With further reference to FIG. 3a, an exemplary embodiment of a method in accordance with the present invention is described. The exemplary method is initiated by setting the RS to zero, where R'' indicates the RS assigned to the current obtained ECG segment and the corresponding acquired CPR reference signal data segment. The ECG segment is preferably obtained at step 110 from electrodes placed on a patient. The CPR reference signal data can be acquired at step 120 from a number of sources, including a thoracic impedance signal obtained from the electrodes, an accelerometer of force sensor signal obtained from a CPR guidance device, or a compressions status signal obtained from an automated CPR machine.

Data from step 120 and/or 110 is next processed at step 130 to detect the presence and level of CPR-related noise on the ECG data set. Several methods have been described in the art to calculate CPR artifact, virtually any of which can be adopted to be used in this step 130. If chest compressions (CC) are detected at step 130, then the RS either remains at zero, or is updated by one unit toward zero, and the algorithm returns to the beginning to process the next data segment. The RS process in the presence of CC is represented by the steps between connectors 'B' and 'G' in the follow-on FIG. 3 illustrations.

If no CPR-related noise is detected, the ECG data set is analyzed for the presence of a shockable cardiac rhythm at step 140. The shock advisory rhythm also can be adopted from one of a number of known methods. The output of analyzing step 140 is passed to classifying step 150 at FIG. 3b, which classifies the ECG data set as a "shock" advice or as a "no-shock" advice. If the analysis indicates the presence of noise-related artifact that can be induced by other than CPR, the output of step 150 can optionally be "artifact."

The first ECG data set classified by step 150 is assigned with an RS of 3 if a shock advice, −3 if a no-shock advice, or 0 if artifact. The exemplary method then proceeds back to the beginning of the process to evaluate the next ECG data set.

Figure 3D:
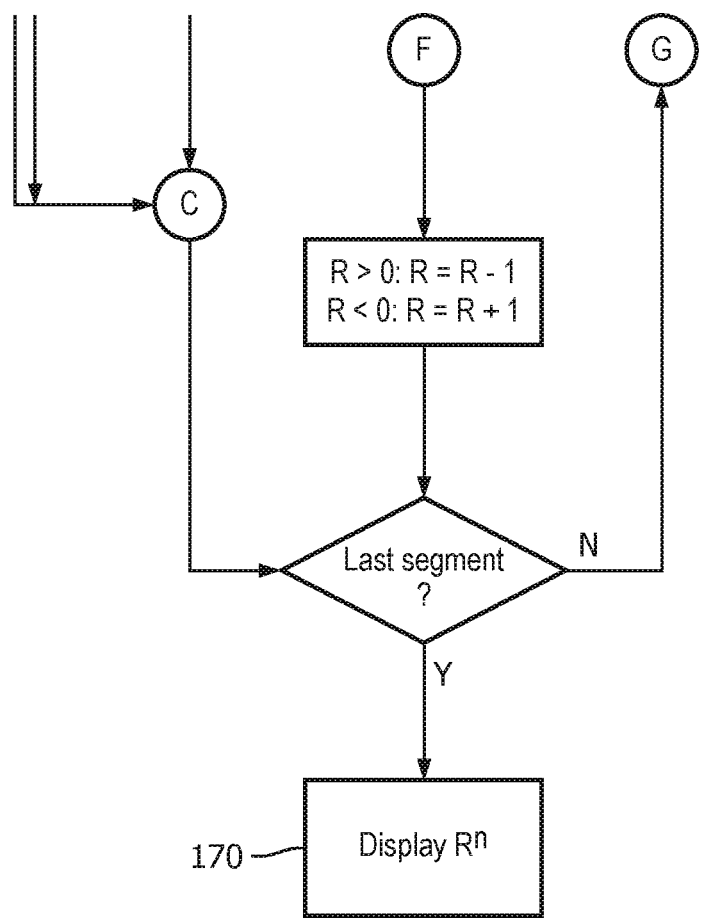

If the ECG data set is the second or later of a stream of ECG data sets, however, step 150 passes the classification to determining step 160 for determining the RS. It can be seen in FIG. 3c that the determining step 160 can use the advice from the current ECG data segment, the advice from the previous ECG data segment, the CC status on the previous ECG data segment and/or the RS from the previous ECG data segment to determine and update the current RS. In accordance with the precepts of the present invention and by inspection of the logic flow in FIG. 3c, it can be seen in this description of an exemplary embodiment of the present invention that a switch in a 'clean', i.e. artifact-free and CPR-noise-free, ECG advice renders the RS score unreliable. A confirming 'clean' ECG data segment improves the RS by one unit up until the maximum, i.e. +6 or −6. A first 'clean' advice results in an RS of either +3 or −3 depending on the nature of the advice. After the RS is determined at step 160, the process automatically outputs the current shock advice and the updated RS to the device at automatically issuing step 170. FIG. 3d illustrates. Preferably, automatically issuing step 170 comprises a display of the current RS. Automatically issuing step 170 can further determine a final shock decision for use by the device, based on the output of classifying step 150 and determining step 160. It should be understood by one having ordinary skill in the art that the final shock decision can be determined from a single or two or more advices. Then the process returns to the beginning via connector 'G' to process the next ECG data segment.

Further, in accordance with exemplary embodiments of the present invention, the display of the current RS in automatically issuing step 170 can be in several different user-perceptible formats. For example, the RS can be displayed as a text message, wherein the RS number is displayed along with a statement to describe the reliability zone in which it falls. As an example, any of the following statements can be shown on the display upon the ECG data segment determination, with or without displaying the RS number:

Reliable Shock Advice
Unreliable Advice
Reliable No-Shock Advice

Preferably, though, the RS is (also) displayed as a graphical indication that can be quickly and easily interpreted by the user. The graphical display is preferably intuitive such that even a user without training or knowledge of the device instructions for use or a physician's guidance document can quickly ascertain whether the shock decision is reliable or not. Shown in FIG. 11a and FIG. 11b are two exemplary embodiments of such a graphical indicator in accordance with the present invention.

For example, FIG. 11a illustrates an exemplary graphical indicator 1100 comprising a pointer graphic 1110 which points to a location on a bar graphic 1120 corresponding to the RS. The bar graphic 1120 is comprised of three segments. Segment 1130 indicates a zone of a reliable shock decision, corresponding in this case to RS scores of +4, +5, and +6. Segment 1130 preferably has a unique color, such as red. Segment 1132 indicates an unreliable decision, corresponding in this case to RS scores ranging from +3 to −3. The unique color of segment 1132 is preferably yellow. Finally, segment 1134 indicates a zone of a reliable no-shock decision, corresponding in this case to RS scores of −4, −5, and −6. Segment 1134 also should have a unique color, such as green.

FIG. 11b illustrates an exemplary RS graphic display 1150 which is similar to exemplary graphic 1100 except for the bar being a speedometer-shaped arc. For example, exemplary graphical indicator 1150 comprises a pointer graphic 1160 which points to a location on a bar graphic 1170 corresponding to the RS. The bar graphic 1170 is comprised of three segments. Segment 1180 indicates a zone of a reliable shock decision, corresponding in this case to RS scores of +4, +5, and +6. Segment 1180 preferably has a unique color, such as red. Segment 1182 indicates an unreliable decision, corresponding in this case to RS scores ranging from +3 to −3. The unique color of segment 1182 is preferably yellow. Finally, segment 1184 indicates a zone of a reliable no-shock decision, corresponding in this case to RS scores of −4, −5, and −6. Segment 1184 also should have a unique color, such as green.

The exemplary method shown in FIGS. 3a-3d is preferably running continuously during the underlying cardiac rescue, whatever device on which it is installed. Optionally, in accordance with exemplary embodiments of the present invention, the exemplary method, in particular the acquiring step 120, detecting step 130, analyzing step 140, classifying step 150, and determining step 160, is conducted only during a protocol CPR period in which the medical device is inoperable to deliver a defibrillation shock. In this optional case, the automatically issuing step 170 occurs immediately after the end of the CPR protocol period. This optional case can be desirable to users who are comfortable with the existing shock advisory protocol and user interface that occurs during electrotherapeutic periods of operation, for example.

Additionally, in accordance with exemplary embodiments of the present invention, the exemplary method illustrated in FIGS. 3a-3d can comprise an additional step, not shown, of adjusting the shock decision protocol used at the analyzing step 140 and/or the issuing step 170 based on the output of the classifying step 150 and the determining step 160. One objective of adjusting the protocol could be to shorten the duration of a shock decision analysis period required to issue a shock decision to the medical device, if the RS is consistently reliable. This could reduce the time to shock, a critical parameter for patient survival. A corresponding objective can be to lengthen the duration of a shock decision analysis period if the RS is consistently unreliable. The duration adjustment could be facilitated by shortening each ECG data segment and/or by reducing the number of ECG data segments needed to make a shock decision, for example.

FIG. 5 is a truth table 500 showing the update of the RS at column 570 for each possible combination of current and preceding ECG data segments and CPR reference signal data sets in accordance with exemplary embodiments of the present invention. For example, the parameters which affect the update of the RS comprise the status of the CC on the current segment 510 and the previous segment 540, the state of the shock advice on the current ECG segment 520 and on the previous ECG segment 550, the RS for the previous ECG data segment 530, and whether or not the current ECG data segment is the first segment of the stream of ECG data 560.

It can been seen in FIG. 5 that the RS for each situation is updated by the previously described exemplary method according to both of the previous and existing segments of ECG and CPR data. For example, if a no-shock advice follows a shock-advice, then the RS is reduced by 7 units to ensure that the RS is displayed in the unreliable zone. A similar situation occurs if a shock-advice follows a no-shock advice. Then, if the new advice is confirmed, the RS gradually becomes more reliable again. Each segment which has artifact or CC causes the RS to become more unreliable by one unit.

FIG. 6 illustrates an exemplary embodiment of a medical device 600 for determining the reliability of a cardiac rhythm analysis during the performance of CPR. In this example, medical device 600 is a defibrillator. The basic functionality of device 600 follows the exemplary method shown in FIGS. 3a-3d. An ECG signal and a CPR reference signal (usually thoracic impedance), as described previously, arrive at the device 600 continuously. A chest compression detection module 608 checks the presence of chest compression (CC) in the ECG fixed-length segments. The CPR reference signal may be also be used for CC detection. A core shock-advisory algorithm module 620 identifies the cardiac rhythm of the ECG segment and provides an advice on the shockability of the cardiac rhythm, e.g. a 'shock', a 'no-shock', or optionally an 'artifact' advice. A reliability analyzer 630 receives the information regarding the presence of the chest compression from detector 608 as well as the shockability of the latest ECG segment from module 620 and updates the reliability score accordingly. The output of the reliability algorithm (reliability score RS) is displayed on the visual output and/or submitted to the decision-making module 640 of the device 600 for taking part in the final decision.

In accordance with exemplary embodiments of the present invention and illustrated in this example, the two required inputs to medical device 600 are ECG and CPR chest compression. Electrodes 602 which are attached to a subject patient detect the patient's ECG signal. The detected ECG signal is passed to an ECG front end 604, where the ECG is processed and digitized into a time-varying data stream. Front end 604 further groups the ECG data stream into time-sequential ECG data sets. In a preferred embodiment, the ECG data sets are 4.5 second segments which sequentially overlap by 0.5 seconds. Each raw, i.e. unfiltered, ECG data set is then output from front end 604 to the shock advisory algorithm module 620.

Further, in accordance with exemplary embodiments of the present invention, the input indicative of CPR compressions activity can be obtained from one of a number of sources. For example, shown in FIG. 6 is a CPR sensor 607, which is typically a puck-like device that is placed between the patient's chest and the CPR-giver's hands. Sensors in the CPR sensor 607, such as force sensors and accelerometers, detect the CPR compressions and provide an input signal to device 600. Alternatively, CPR sensor 607 can be a compressions status signal that is obtained from an automated CPR machine. The automated CPR machine may provide an input indicative of the start of a CPR compression, for example.

A preferred second input indicative of CPR is shown in FIG. 6 by the thoracic impedance sensing channel 606. Many devices which monitor ECG also develop an impedance measurement across electrodes 602, in order to assess noise on the ECG signal, to detect patient motion, or to optimize electrotherapy parameters. Here, the impedance measurement is obtained at impedance channel 606 in order to provide the CPR input. This source of CPR input can be advantageous because no additional hardware is typically required, saving rescue time and expense.

However it is detected, in accordance with exemplary embodiments of the present invention, the input indicative of CPR compressions is provided to compression detector 608, where the input is initially digitized into a stream of time-varying CPR reference signals that indicate the frequency of chest compressions. Compression detector 608 further groups the digitized CPR signals into time-sequential CPR data sets. In a preferred embodiment, the CPR data sets are 4.5 second segments which sequentially overlap by 0.5 seconds. Each CPR data set corresponds in time to an ECG data set.

Compression detector 608 can utilize one of a number of known techniques to determine whether the corresponding ECG data set contains CPR-related noise. Detector 608 then outputs the determination as a preferably binary indicator, i.e. chest compressions present (CC) or not (clean). The determination is provided to shock advisory algorithm module 620 and reliability analyzer 630.

Shock advisory algorithm module 620 applies an analysis algorithm to each ECG data set, and classifies each data set as a "shock" or a "no-shock" rhythm, referred to here as an advice. If the data set cannot be classified, the set may optionally be classified as "artifact." The analysis algorithm is as described in the foregoing exemplary method discussion and can be one of several known methods.

A shock decision generator 640 uses the output from the shock advisory algorithm module 620 to determine a final shock decision. A single advice is generally considered to be insufficiently robust to make the final decision in most cases. Some methods require two consecutive shock advices to make a final decision, or two out of three advices to do so.

The reliability analyzer 630 utilizes the previously described exemplary method to determine the reliability of the most recent advice with input from the chest compression detector 608 and the shock advisory algorithm module 620. The output of reliability analyzer 630 is an RS score which can be provided to a user via output generator 650. Optionally, the output of reliability analyzer 630 can also be used by the shock decision generator 640 as a parameter in determining a final shock decision, for example by modifying the number duration of advices prior to making the decision.

Output generator 650 converts the decision output command from shock decision generator 650 into an actionable issued command. If, for example, the decision output command is "arm", output generator 650 controls the device 600 to automatically begin arming a high voltage electrotherapy circuit, such as HV delivery circuit 680. HV delivery circuit 680 is further enabled to deliver a defibrillation shock to the patient via electrodes 602.

Output generator 650 provides an indication of the reliability of the ECG shock advice, preferably via display 660 and/or via audible alerts. The indication, if displayed, is preferably a graphical indicator, but can also comprise a textual message. Output generator 650 can also generate a user-perceptible indication of the shock decision, such as appropriate audible and visual indicators at display 660. This alerts the rescuer as to the actionable command.

In accordance with exemplary embodiments of the present invention, exemplary device 600 can be disposed as a stand-alone device, or can be integrated into another medical device and/or system. For example, exemplary medical device 600 can be incorporated into a patient monitoring system for alerting medical personnel to changes in cardiac rhythm during CPR. Exemplary device 600 can also be integrated with a CPR assistance device which uses CPR sensor 607. It is contemplated and considered to be within the scope of the present invention, that exemplary device 600 can also be used with an automated CPR machine, wherein the input to compression detector 608 could also be a machine compressions status signal and the output from the output generator 650 could control changes in the machine operation. A preferred use/implementation for exemplary device 600 is as a component within a defibrillator or AED, wherein output generator 650 provides control for the arm function of a high voltage delivery circuit 680 based on the need to deliver a defibrillating shock, controls the user interface to guide the user through a cardiac rescue, and optionally automatically delivers the shock through electrodes 602.

The following three examples are provided to further illustrate the functionality of a method according to exemplary embodiments of the present invention. In these following examples, the ECG signal is divided into fixed-length consecutive segments. The outputs of chest compression detector module and the core shock-advisory algorithm for each segment are shown as calculated at the end of each segment. Segments with chest compression artifact on the ECG signal are marked by 'CC', shock-advised segments are noted by 'Sh', no-shock-advised segments are marked by 'NS', and the segments with other types of artifact are marked by 'A'. The reliability score RS is updated according to these data as mentioned in the previous section.

FIG. 7 illustrates an example 700 in accordance with exemplary embodiments of the present invention wherein an underlying non-shockable cardiac rhythm is periodically contaminated by CPR CC noise. The status of chest compressions in each ECG segment is shown in series 702. The shock advices on each ECG segment are shown in series 704. And the RS determined at the end of each ECG segment is shown in series 706. As shown in FIG. 7, after a long series of chest compression segments, the reliability score goes to zero. By stopping the chest compression during quiet period 710 and receiving 'no-shock' advices, the score moves towards the negative values until the RS is the minimum −6. When chest compressions resume, the RS tends back to zero and this cycle repeats. As seen, the segment right after chest compression removal is still unreliable. Following segments become reliable up to the second segment right after the resumption of chest compressions.

FIG. 8 illustrates another example 800 in accordance with exemplary embodiments of the present invention wherein an underlying non-shockable cardiac rhythm is periodically contaminated by CPR CC noise. The status of chest compression in each ECG segment is shown in series 802. The shock advices on each ECG segment are shown in series 804. And the RS determined at the end of each ECG segment is shown in series 806. Shown in FIG. 8 is a series of 'no-shock' advices during chest compressions where the reliability score is zero. Upon stopping chest compressions during quiet period 810, the RS leans towards negative values and enters the reliable no-shock zone after one ECG segment. But then the underlying cardiac rhythm changes to a shockable rhythm during period 820. After determining a first 'shock' advice, the score starts moving towards positive values and enters the reliable shock zone after three unreliable segments. Shock is applied to the patient at the end of period 820 (the segment determined 'artifact' by shock-advisory algorithm), whereupon the rhythm becomes non-shockable again during period 810 and enters the reliable no-shock zone.

FIG. 9 illustrates yet another example 900 in accordance with exemplary embodiments of the present invention wherein an underlying non-shockable cardiac rhythm is periodically contaminated by CPR CC noise. The status of chest compression in each ECG segment is shown in series 902. The shock advices on each ECG segment are shown in series 904. And the RS determined at the end of each ECG segment is shown in series 906. Seen in FIG. 9 is a series of ECG segments in which chest compressions (CC), such as period 920, drive the reliability score to zero. A single non-shockable hands-off segment keeps the score in unreliability zone, while a series of forthcoming non-shockable hands-off segments during quiet periods 910 move the RS to the reliable no-shock zone. There is no 'shock' advice during these hands-off intervals.

Now turning to FIG. 10, a exemplary embodiment of a defibrillator 1000 in accordance with the present invention is illustrated which incorporates the reliability scoring functionality as previously described. In this exemplary embodiment, defibrillator 1000 is an automatic external defibrillator (AED) which comprises an electrode connector socket 1050 to which patient monitoring and defibrillation electrodes are connected. Socket 1050 is thus the source of the ECG data and the CPR data. A status indicator 1040 continuously provides the operational status.

Defibrillator 1000 also comprises a number of user interface elements. For example, an illuminated shock button 1060 is provided to enable the user to deliver a shock after the device arms itself. A speaker 1070 issues audible guidance and commands, such as whether a shock is advised or not. A display 1020 is provided upon which the RS graphic is displayed to the user. Various user controls 1030 can be provided to manipulate other functionality of the AED.

In accordance with exemplary embodiments of the present invention, the internal circuitry of defibrillator 1000 is disposed as a host circuit 670, shown in FIG. 6, which runs in concert with reliability analyzing circuit 630. The reliability analysis algorithm resides on circuit 630, while the core shock-advisory algorithm module and the chest compression detector reside on host circuit 670. Alternatively, those two modules can be implemented as parts of the reliability algorithm circuit 630.

As shown, host circuit 670 operates to analyze the received ECG segment(s) and to determine whether a defibrillating shock is necessary. Reliability analyzing circuit 630 simultaneously operates to determine a reliability of the host circuit determination, based on the current and a prior analysis of the ECG segment. An RS is generated from the reliability determination, which is then displayed on display 1020. The nature of the graphic display is preferably similar to that shown in FIG. 11*a* or 11*b*, as previously described.

One having ordinary skill in the art should appreciate in view of the teachings provided herein that modifications to the device as described herein with reference to the appended figures are encompassed within the scope of the invention. For example, several or all of the individual circuits shown in FIG. 6 may be integrated together into a single controller or processor in order to reduce complexity and space. In particular, each of the host computer functions and reliability analyzer functions can be implemented as a single software module. Alternatively, some described function(s) of the individual circuits can be performed by other of the circuits. A separate analog-digital conversion circuit, for example, could be dedicated to provide all of the pre-processing of ECG and CPR inputs. Variations in the nature and names of the outputs, which fulfill essentially the same user interface and device control objectives, also fall within the scope of the invention.

Further, as one having ordinary skill in the art will appreciate in view of the teachings provided herein, features, elements, components, etc. described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figure can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read-only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments for systems, devices, and methods for monitoring a subject cardiac rhythm during the application of cardio-pulmonary resuscitation (CPR) (which embodiments are intended to be illustrative and not limiting), it is noted that modifications and variations can be made by persons skilled in the art in light of the teachings provided herein (including the appended Figures). It is therefore to be understood that changes can be made in/to the preferred and exemplary embodiments of the present disclosure which are within the scope of the embodiments disclosed herein.

What is claimed is:

1. A medical device for determining the reliability of a cardiac rhythm analysis during the performance of cardiopulmonary resuscitation (CPR) comprising:
a front end operable to obtain two or more time-sequential ECG data sets comprised of a first ECG data set and a second ECG data set;
an input sensor operable to acquire two or more time-sequential CPR reference signal data sets which correspond in time to the time-sequential ECG data sets;
a chest compression detector in communication with the input, operable to detect whether or not each of the ECG data sets contains CPR-related noise;
a shock advisory algorithm module in communication with the input and the chest compression detector and operable to analyze and classify each of the ECG data sets that do not contain CPR-related noise as a shock advice or a no-shock advice;
a reliability analyzer in communication with the chest compression detector and the shock advisory algorithm module operable to determine the reliability of the most recent shock or no-shock advice, wherein the reliability analyzer is configured to generate a reliability score at the end of each of the ECG data sets by operations including:
responsive to a number of consecutive ECG data sets that do not contain CPR-related noise being similarly classified as the shock advice, the reliability analyzer is configured to update a value of the reliability score in a direction corresponding to the shock advice until the reliability score reaches a scoring limit corresponding to the shock advice;
responsive to a number of consecutive ECG data sets that do not contain CPR-related noise being similarly classified as the no-shock advice, the reliability analyzer is configured to update the value of the reliability score in a direction corresponding to the no shock advice until the reliability score reaches a scoring limit corresponding to the no shock advice;
responsive to the most recent ECG data set not containing CPR-related noise and being classified as a switched shock or no shock advice, the reliability analyzer is configured to update the value of the reliability score toward a score value indicating an indeterminate condition; and
responsive to the most recent ECG data set containing CPR-related noise, the reliability analyzer is configured to update the value of the reliability score toward the score value indicating the indeterminate condition;
a shock decision generator in communication with the reliability analyzer and the shock advisory algorithm module operable to generate a shock decision based on the reliability score; and
an output generator for issuing a user-perceptible indication of the shock decision and the reliability of the ECG shock advice.

2. The medical device of claim 1, wherein the medical device is a defibrillator.

3. The medical device of claim 1, wherein the shock advisory algorithm module is further operable to analyze and classify each of the ECG data sets as artifact.

4. The medical device of claim 1, wherein the output generator comprises a display disposed in communication with the medical device operable to display an indication of the reliability of the ECG shock advice.

5. The medical device of claim 4, wherein the displayed indication of the reliability of the ECG shock advice comprises a graphical indicator.

6. The medical device of claim 4, wherein the displayed indication of the reliability of the ECG shock advice comprises a textual message.

7. The medical device of claim 1, wherein the reliability analyzer determines the reliability of the most recent ECG device based on a determined reliability of the previous ECG data set.

8. The medical device of claim 1, wherein the shock decision generator is further operable to adjust a shock decision protocol based on a classification by the shock advisory algorithm module of each of the ECG data sets as a shock advice or a no-shock advice and further based on a determination by the reliability analyzer of the reliability of the most recent ECG advice.

9. The medical device of claim 8, wherein the shock decision generator adjusts the shock decision protocol by reducing a duration of a shock decision analysis period for generating the shock decision.

10. The medical device of claim 1, wherein responsive to the number of consecutive ECG data sets being similarly classified as the shock advice and the reliability score reaching the threshold reliability score, the shock decision generator is configured to generate a shock decision.

11. The medical device of claim 10, wherein responsive to the shock decision being generated by the shock decision generator, the output generator is configured to automatically arm a high voltage electrotherapy circuit, the high voltage electrotherapy circuit configured to deliver a defibrillation shock to a patient.

12. The medical device of claim 1, wherein the input sensor comprises one or more of patient electrodes, a force sensor, or an accelerometer.

13. A defibrillator comprising:
a host circuit operable to analyze ECG segments and determine whether each ECG segment is a clean ECG segment that does not contain chest compressions-related noise and to make a shock determination decision for each clean ECG segment;
a reliability analyzing circuit operable to analyze each ECG segment to generate a reliability score at the end of the ECG segment by operations including:
for each clean ECG segment that has a shock determination decision confirming the shock determination decision for the last clean ECG segment, updating the reliability score in a direction corresponding to the confirming shock determination decision until the reliability score reaches a scoring limit corresponding to the confirming shock determination decision;
for each switched clean ECG segment that has a shock determination decision opposite to the shock determination decision for the last clean ECG segment, updating the reliability score toward a score value indicating an indeterminate condition; and
for each ECG segment that is not a clean ECG segment, updating the reliability score toward the score value indicating the indeterminate condition; and
a display disposed on the defibrillator operable to display the generated reliability score.

14. The defibrillator of claim 13, wherein the displayed reliability score is a textual indication of whether or not the shock decision is reliable.

15. The defibrillator of claim 13, wherein the displayed reliability score is a graphical indicator disposed as a pointer graphic which points to one segment of a three-segment bar graphic, wherein one of the segments indicates a reliable no-shock decision, another one of the segments indicates an unreliable decision, and another one of the segments indicates a reliable shock decision.

16. The defibrillator of claim 15, wherein the three-segment bar graphic comprises one color for the unreliable segment and another color for the reliable segments.

17. The defibrillator of claim 13, further comprising a high voltage electrotherapy circuit configured to deliver a defibrillation shock to a patient responsive to the shock determination decision being a shock decision and the reliability score reaching the scoring limit corresponding to the confirming shock determination decision.

18. A defibrillator comprising:
   a computer programmed to analyze ECG segments and determine whether each ECG segment is a clean ECG segment that does not contain chest compressions-related noise and to make a shock determination decision for each clean ECG segment, and further programmed to analyze each ECG segment to generate a reliability score at the end of the ECG segment by operations including:
     for each clean ECG segment that has a shock determination decision confirming the shock determination decision for the last clean ECG segment, updating the reliability score in a direction corresponding to the confirming shock determination decision until the reliability score reaches a scoring limit corresponding to the confirming shock determination decision;
     for each switched clean ECG segment that has a shock determination decision opposite to the shock determination decision for the last clean ECG segment, updating the reliability score toward a score value indicating an indeterminate condition; and
     for each ECG segment that is not a clean ECG segment, updating the reliability score toward the score value indicating the indeterminate condition;
   a display disposed on the defibrillator operable to display a representation of the most recently generated reliability score; and
   a high voltage electrotherapy circuit configured to deliver a defibrillation shock to a patient in accordance with the shock determination decisions.

* * * * *